United States Patent
Omura et al.

(10) Patent No.: US 6,734,292 B1
(45) Date of Patent: May 11, 2004

(54) PSEUDOERYTHROMYCIN DERIVATIVES

(75) Inventors: Satoshi Omura, Tokyo (JP); Yuzuru Iwai, Tokyo (JP); Toshiaki Sunazuka, Tokyo (JP); Tohru Nagamitsu, Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/088,965

(22) PCT Filed: Aug. 17, 2000

(86) PCT No.: PCT/JP00/05503

§ 371 (c)(1),
(2), (4) Date: Jul. 25, 2002

(87) PCT Pub. No.: WO02/14338

PCT Pub. Date: Feb. 21, 2002

(51) Int. Cl.[7] .............................................. C07H 17/08
(52) U.S. Cl. ........................ 536/7.2; 536/7.3; 536/17.2; 536/17.5
(58) Field of Search .................... 536/7.2, 7.3, 17.2, 536/17.5, 7.1, 7.4

(56) References Cited

U.S. PATENT DOCUMENTS

| | | | |
|---|---|---|---|
| 4,920,102 | A | 4/1990 | Gidda et al. |
| 5,106,961 | A | 4/1992 | Kirst et al. |
| 5,418,224 | A | 5/1995 | Hoeltje et al. |
| 5,523,401 | A | 6/1996 | Freiberg et al. |
| 5,523,418 | A | 6/1996 | Freiberg et al. |
| 5,538,961 | A | 7/1996 | Freiberg et al. |
| 5,554,605 | A | 9/1996 | Freiberg et al. |
| 5,912,235 | A | 6/1999 | Hoeltje et al. |

FOREIGN PATENT DOCUMENTS

| | | |
|---|---|---|
| EP | 0 296 717 | 12/1988 |
| EP | 0 937 734 A1 | 8/1999 |

OTHER PUBLICATIONS

J. Japan. Thorac. Dis. Assoc., Kudo et al., "Studies of Clinical Results on Long Term Small Administration of Erythromycin for Diffuse Panbronchiolitis–Treatment Results for 4 Years", 1987, pp. 632–642.

Iyaku Journal Inc., Osaka, Kudo et al., "Inflammation, Immunit and Macrolides up to Date", 1996.

J. Org. Chem., Kirst et al., "Synthesis of Ring–Contracted Derivatives of Erythromycin", 1987, pp. 4359–4362.

Am J. Respir. Crit. Care Med., Sato et al., "Therapeutic Effect of Erythromycin on Influenza Virus–Induced Lung Injuryin Mice", vol. 157, 1998, pp. 853–857.

Throax, Azuma et al., "Preventive Effect of Erythromycin on Experimental Bleomycin–Induced Acute Lung Injury in Rats", vo.. 53, No. 3, 3/98, pp. 186–189.

J. Org. Chem., Kibwage et al., "Translactionization in Erythromycins", 1987, pp. 990–996.

The Journal of Antibiotics, Keicho et al., "Erythromycin Promotes Monocyte to Macrophage Differentiation", vol. 52, Jan. 1994, pp. 80–89.

*Primary Examiner*—Elli Peselev
(74) *Attorney, Agent, or Firm*—Young & Thompson

(57) ABSTRACT

The present invention is to obtain novel anti-inflammatory agents having decreased antibacterial activity and increased anti-inflammatory action, and is psedoerythromycin derivatives represented by the following general formula [I],

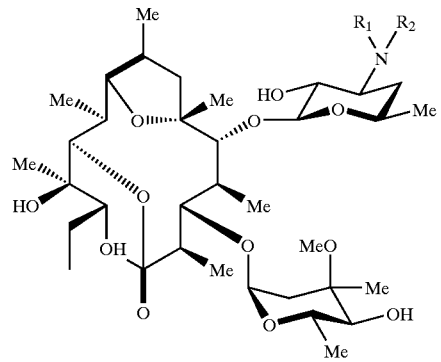

wherein R1 and R2 are same or different and each represents H, alkyl, alkynyl, acyl or sulfonyl, in which these groups may optionally have substituents, and Me indicates methyl.

30 Claims, 3 Drawing Sheets

FIG. 1
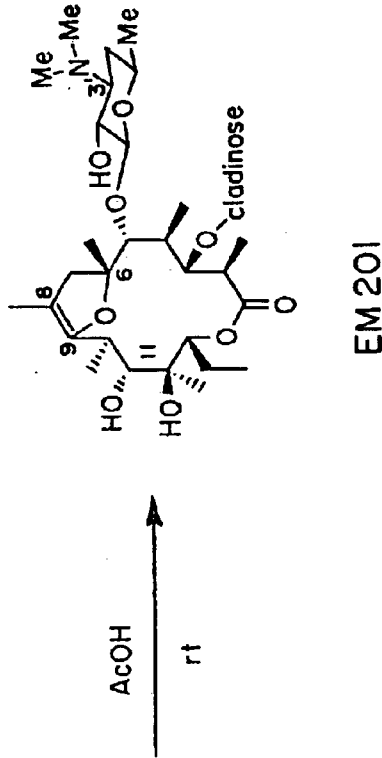
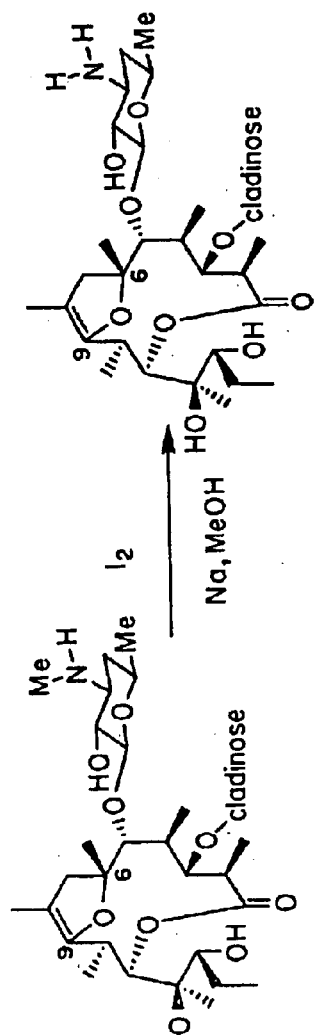
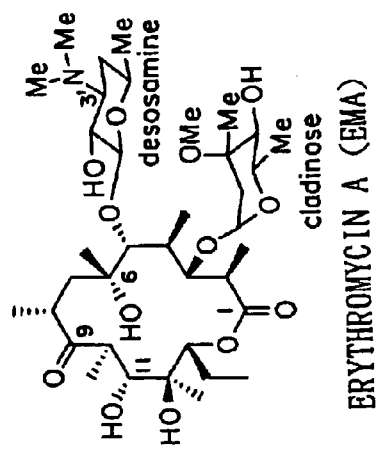
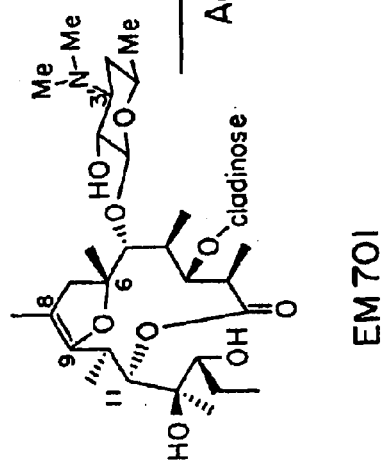

PSEUDOERYTHROMYCIN DERIVATIVES

BACKGROUND OF THE INVENTION

1. Field of the Invention

The present invention relates to novel pseudoerythromycin derivatives or salt thereof.

2. Description of Related Art

Erythromycin (hereinafter sometimes designates as EM) has been used for long time as 14-membered macrolide antibiotic for treatment of infectious disease caused by Gram-positive bacteria. During past ten and several years, erythromycin has known to improve long-term chronic inflammatory diseases such as diffuse panbronchiolitis and bronchial asthma, except for therapeutic action to bacterial infectious diseases. (Kudo, Shojli et al., Studies of clinical results on long term small administration of erythromycin for diffuse panbronchiolitis-Treatment results for 4 years, J. Japan. Thorac. Dis. Assoc., 25: 632–642, 1987).

Erythromycin is an antibiotic and has antibacterial action which is not always required for treatment of inflammatory diseases. Consequently, resistant bacteria are generated in patients who are administered antibiotics, as a result, it causes deterioration for treatment of infectious disease in the other occasion.

As described above, Kudo, Shoji et al. demonstrated that diffuse panbronchiolitis could be improved by long term small administration of erythromycin (Kudo, Shoji et al., Studies of clinical results on long term small administration of erythromycin for diffuse panbronchiolitis-Treatment results for 4 years, J. Japan. Thorac. Dis. Assoc., 25: 632–642, 1987).

SUMMARY AND OBJECT OF THE INVENTION

Recently, actions other than antibiotic activity of erythromycin is noted, as a result, usefulness other than pulmonary region, for example not limited in diffuse panbronchiolitis but for chronic sinusitis and Crohn's disease are reported. The mechanism of action of erythromycin for chronic disease such as diffuse panbronchiolitis is thought to be the result of original antibacterial action. Research studies are now ongoing, and indicate the antiinflammatory action mediated by immune inflammatory cells in the penumbral chronic respiratory tract inflammation.

For example, the studies indicate the regulation for migration of neutrophils to infectious region by direct action, and the regulation for migration of neutrophils or for release of active oxygen from neutrophils by indirect action through mediators or cytokines. Further, erythromycin has an action to lymphocytes, macrophages and mast cells to regulate their proliferation or cytokine production, or to induce differentiation. (Kudo, Shoji Ed., Supervisors: Shimizu, Kihachiro and Omura Satoshi "Inflammation, Immunity and Macrolides Up to Date", Iyaku Journal Inc., Osaka, 1996)

As explained above, 14-membered macrolides are thought to cure chronic respiratory diseases as a result of exhibiting immune regulation and antiinflammatory action.

We have aimed at the promoting action of erythromycin for differentiation-induction frommonocyte to macrophage (N. Keicho, S. Kudoh, H. Yotsumoto, K. Akagawa, "Erythromycin promotes monocyte to macrophage differentiation", J. Antibiotics, 47, 80–89, 1994), and tried to synthesize erythromycin derivatives for the purpose of creating the derivatives having disappeared antibacterial action and enhanced promoting action for differentiation-induction.

The present invention relates to a novel pseudoerythromycin derivative represented by the general formula [I],

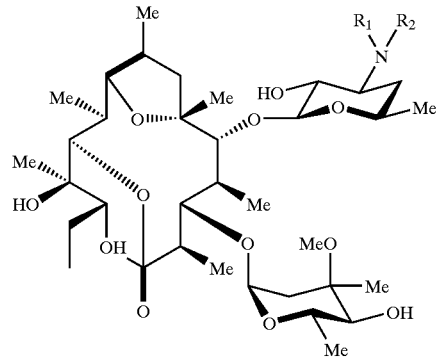

wherein $R_1$ and $R_2$ are same or different and each represents H, alkyl, alkynyl, acyl, or sulfonyl, in which these groups may optionally have substituents, and Me indicates methyl.

Further, the present invention relates to a novel pseudoerythromycin derivative represented by the general formula [II],

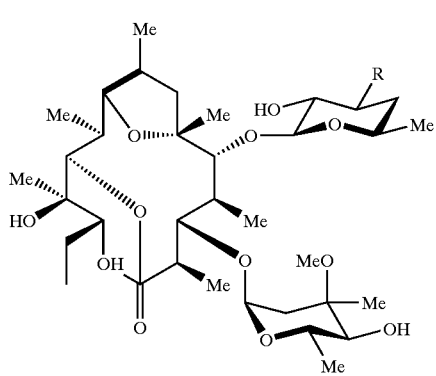

wherein R is heterocyclic containing N which may optionally have substituents, and Me indicates methyl.

The present invention further relates to a novel pseudo erythromycin derivative represented by the general formula [III],

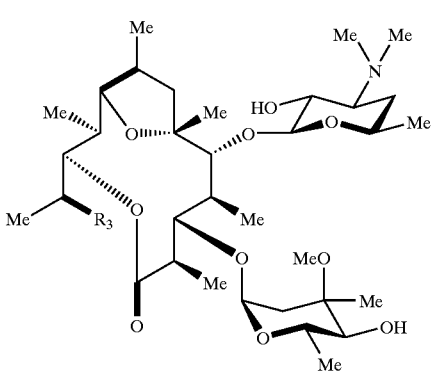

wherein $R_3$ is O or NOH, and Me indicates methyl.

The invention further relates to a novel pseudoerythromycin derivative represented by the general formula [IV],

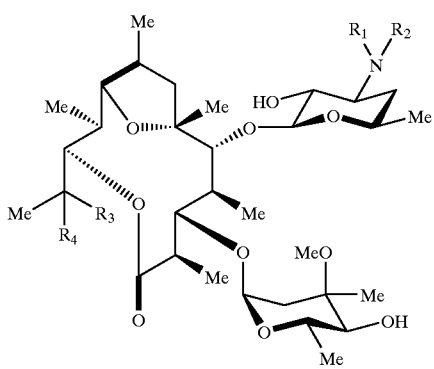

[IV]

wherein $R_1$ and $R_2$ are same or different and each represents H or methyl, $R_3$ and $R_4$ represent H, hydroxyl or amino, and Me indicates methyl.

The present invention further relates to a novel pseudo erythromycin derivative represented by the general formula [V],

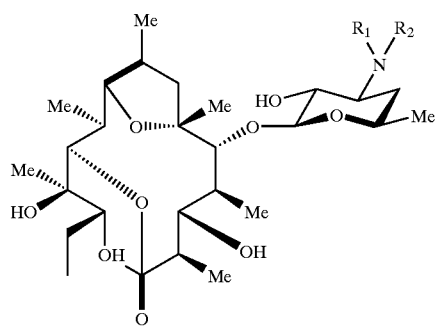

[V]

wherein $R_1$ and $R_2$ are same or different and each represents H or methyl, and Me indicates methyl.

Synthetic methods of various erythromycin derivatives are, for example, illustrated in the synthetic scheme as shown in FIG. 1. Namely, erythromycin A is treated with ice-cold acetic acid according to the references: (a) I. O. Kibwage, R. Busson, G. Janssen, J. Hoogmartens, H. Vanderhaeghe, Translactonization of Erythromycins, J. Org. Chem., 52, 990–996, 1987, (b) H. A. Kirst, J. A. Wind, J. W. Paschal, Synthesis of Ring-Constracted Derivatives of Erythromycin, J. Org. Chem., 52, 4359–4362, 1987, introducing to erythromycin A enol ether (EM 201), subsequently refluxing in methanol with heating in the presence of potassium carbonate to introduce pseudoerythromycin A enol ether (EM701) (known compound).

The product was treated with iodine and sodium acetate according to the reference (L. A. Friberg, U.S. Pat. No. 3,725,385) to obtain de-N-methyl-pseudoerythromycin A enol ether (EM703) (known compound). The compound was further treated with iodine and sodium methoxide to obtain bis(de-N-methyl)-pseudo erythromycin A enol ether (EM721) (novel compound). Alkylation, acylation and sulfonylation using EM703 and EM721 resulted to synthesize various derivatives through bis-de(3'-N-methyl)-3'-N-ethyl-8,9-anhydro-pseudoerythromycin A 6,9-hemiketal (EM722).

The synthetic scheme of compounds of the present invention is illustrated in FIG. 1. Namely, the compounds can be obtained by the synthetic route of: erythromycin A (EMA) →erythromycin A enol ether (EM201) →pseudoerythromycin A enol ether (EM701)→de-N-methyl-pseudoerythromycin A enol ether (EM703)→bis(de-N-methyl)-pseudoerythromycin A enol ether (EM721).

In order to confirm enhancing effect for differentiation-induction of the compounds of the present invention, the enhancing effect for differentiation-induction from human monocyte to macrophage was assayed. Method is performed as follows.

THP-1 cells were collected from cultured liquid by centrifugation, adjusted the concentration to $2\times10^5$ cells/ml using medium (RPMI 1640) and distributed into the 48-well plate at 500 $\mu$l/well. PMA solution 10 $\mu$l and sample solution 5 $\mu$l were added in each well, stirred with mild shaking and incubated at 37° C. for 72–96 hours under 5% $CO_2$. Further MTT 0.5 mg/ml solution was added at 300 $\mu$l/well, and incubated at 37° C. for 3 hours under 5% $CO_2$. Supernatant solution was suctioned using the injection tube, added DMSO 500 $\mu$l using automatic continuous injector to dissolve formazan completely and transferred each 100 $\mu$l to the 96-well plate. The optical absorption was measured using the plate-reader.

Results of the enhancing effect for differentiation-induction from human monocyte to macrophage measured by the above assay method are shown in Table 1.

TABLE 1

Structure of EM703 analogous derivatives and activities in THP-1/M$\phi$ system

| EM | Others $R_1$ | $R_2$ | Treated conc. ($\mu$M) 0.3 | 1 | 3 | 10 | 30 | $ED_{50}$ ($\mu$M)* |
|---|---|---|---|---|---|---|---|---|
| 703 | Me | H | + | + | + | + | / | 0.3 |
| 721 | H | H | NT | NT | − | + | / | 10 |
| 722 | Et | H | − | + | + | ++ | / | 1 |
| 723 | Et | Et | − | + | + | | / | 1 |
| 724 | Allyl | H | − | + | + | ++ | / | 1 |
| 725 | Allyl | Allyl | NT | − | ± | + | / | 3 |
| 726 | Ac | H | − | − | − | − | − | — |
| 727 | Ms | Me | − | + | + | + | / | 1 |
| 728 | $CH_2C\equiv CH$ | H | − | + | + | + | + | 1 |

TABLE 1-continued

Structure of EM703 analogous derivatives
and activities in THP-1/Mφ system

| | Others | | Treated conc. (μM) | | | | | $ED_{50}$ (μM)* |
|---|---|---|---|---|---|---|---|---|
| EM | $R_1$ | $R_2$ | 0.3 | 1 | 3 | 10 | 30 | |
| 729 | $CH_2C{\equiv}CH$ | $CH_2C{\equiv}CH$ | − | ± | ± | ± | / | 1 |
| 730 | Pr | H | + | + | + | / | / | 0.3 |
| 731 | Pr | Pr | − | − | + | / | / | 3 |
| 732 | Bn | H | + | + | + | + | / | 0.3 |
| 733 | Bn | Bn | − | ± | ± | / | / | 1 |
| 734 |  | | − | ± | + | + | / | 1 |
| 735 |  | | − | ± | + | ++ | / | 1 |
| 736 | i-Pr | H | − | ± | + | ++ | / | 1 |
| 737 | Me | Me decladinose | NT | NT | − | + | / | 10 |
| 738 | $C_6H_{13}$ | H | − | ± | + | / | / | 1 |
| 739 | $C_6H_{13}$ | $C_6H_{13}$ | − | ± | + | + | / | 1 |
| 740 | $C_2H_4F$ | Me | ± | ± | + | + | + | 0.3 |
| 742 | $CH_2CN$ | Me | − | − | − | + | + | 10 |
| 743 | Me | Me Cl2oxime | NT | − | ± | − | / | — |
| 744 | $C_3H_6OH$ | Me | NT | − | − | − | / | — |
| 745 | $C_2H_4OAc$ | Me | − | − | ++ | ++ | ++ | 3 |
| 746 | Me | Me Cl2MeCHOH | − | ± | + | + | + | 1 |
| 747 |  | | NT | NT | − | ± | ++ | 10 |
| 748 |  | | − | ± | ++ | ++ | / | 1 |
| 749 | $(CH_2)_{10}Br$ | $(CH_2)_{10}Br$ | NT | ± | + | + | /insolule | 1 |
| 750 | Me | Me Cl2MeCHNH$_2$ | NT | − | − | ± | / | 10 |
| 751 | H | Me Cl2MeCHOH | ± | ± | + | + | / | 0.3 |
| 754 | Me | H decladinose | NT | − | − | NT | + | 30 |
| EM | Me | M1 | NT | − | ± | + | + | 3 |
| CAM | Me | M1 | NT | NT | − | + | − | 10 |
| EM oxim | Me | Me C9oxime | NT | − | ± | ± | ++ | 3 |

In Table 1: Me: methyl; Pr: propyl; Et: ethyl; Ac: acetyl; and Ms: methanesulfonyl. *$ED_{50}$: Drug concentration (μM) required for 50% differentiation-induction of THP in Mφ.

In Table 1, indicated activity is represented in comparison with enhancing action for differentiation-induction of EM 100 μM and symbols are: ++: enhanced 100% or more; +: enhanced 50–100%; ±: enhanced 25–50%; −: no activity; /: expressed cytoxicity; and NT: not tested or under assessment.

As shown in Table 1, since the smaller the value of $ED_{50}$ (μM), (minimum drug concentration required for 50% differentiation-induction from THP-1 to Mφ), the stronger the differentiation-induction activity, it was found that the compounds of the present invention have enhancing action for diffferentiation-induction from THP-1 to Mφ.

Next, the suppressive effect of the compound of the present invention (EM703) against bleomycin-induced pulmonary fibrosis was examined (hereinafter sometimes designates bleomycin as BLM).

A sample suspended in 5% gum arabic was orally administered, 50 mg/kg/day for 17 days (from day-3 to day-13), and bleomycin, 100 mg/kg, was administered from tail vein in day-0. On day-28, animals were sacrificed under anesthesia and fibrosis of the lungs was compared with non-administered mice. Suppressive effects are shown in Table 2.

References

Azuma A., Furuta T., Enomoto T., Hashimoto Y., Uematsu K., Nukariya N., Murata A., Kudoh S., Preventive effect of erythromycin on experimental bleomycin-induced acute lung injury in rats Thorax 53, 186–189, 1998

TABLE TWO

[Administration schedule]

BLM 100 mg/kg
↓
Day −3 −2 −1 0 1 2 3 4 5 6 7 8 9 10 11 12 13 14 28
    EM703 50 mg/kg/day                                ↓
                                                 sacrificed Results: Hydroxyproline levels in tissue

| Group | | Assay result (μmol/l) | Weight conversion (μmol/g) |
|---|---|---|---|
| Cont |  | 440 | 4.0 |
| BLM | 1 | 785 | 7.1 |
| BLM | 2 | 733 | 6.4 |
| EM703 | 1 | 552 | 5.0 |
| EM703 | 2 | 489 | 4.6 |
| EM703 | 3 | 591 | 5.4 |
| BLM + EM703 | 1 | 583 | 5.2 |
| BLM + EM703 | 2 | 495 | 4.5 |
| BLM + EM703 | 3 | 437 | 4.4 |
| BLM + EM703 | 4 | 314 | 2.9 |
| BLM + EM703 | 5 |  |  |

Group:
Cont (control) group (n = 1)
BLM (bleomycin) group (n = 2)
EM (erythromycin) group (n = 4)
BLM (bleomycin) + EM (erythromycin) 703 group (n = 5)

As indicated above, hydroxyproline is an index of lung fibrosis and higher value indicates hyperfibrosis. Hydroxyproline level, an index for lung injury, in BLM administered group was reduced in a group of BLM+EM703.

Next, the suppressive effect of the compound EM703 against pneumonia caused by influenza viral infection was examined.

Sample was dissolved in physiological saline containing 1% DMSO and amount corresponding to oral dosage of the small administration for long-term therapy was administered from day-1 to day-6 of the infection to mice influenza pneumonia model (0.3 mg and 0.03 mg/mice), once a day, intraperitoneally. Results were compared with control group which was given only solvent.

Reference

Sato K., Suga M., Akaike T. et al., Therapeutic effect of erythromycin on influenza virus-induced lung injury in mice. Am. J. Respir Crit. Care Med. 157, 853–859, 1998.

Results are shown in FIG. 2 and FIG. 3. In this system, mice developed pneumonia and almost died about 20 days after infection. Contrary to that, as shown in FIG. 2, administration of EM703, 0.3 mg/mice, cured pneumonia and 40% of mice were survived. Further, as shown in FIG. 3, mice without administration of drugs (control) indicated significant decrease of body weight due to pneumonia, but administration of EM703 indicated to increase body weight from day-10. This indicates suppressive effect against pneumonia and result to cure pneumonia.

As described above, the compound of the present invention shows suppressive effect against influenza virus-induced pneumonia.

BRIEF DESCRIPTION OF THE FIGURES

FIG. 1 shows an example of the synthetic scheme of the compound of the present invention.

DETAILED DESCRIPTION OF PREFERRED EMBODIMENTS

Figure 2:
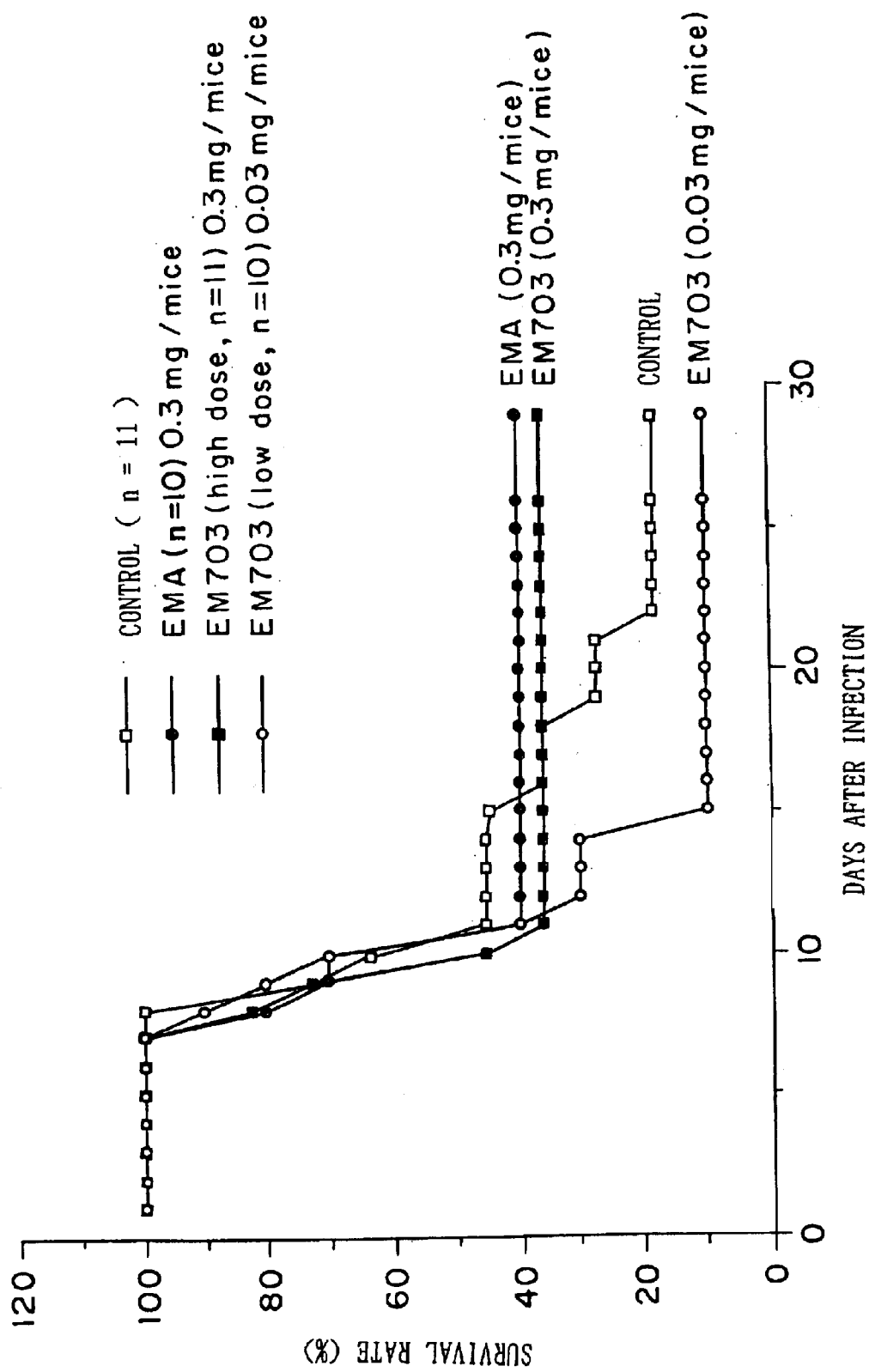
FIG. 2 is a graph of the suppressive effect against pneumonia showing relationship between numbers of day after infection due to influenza virus infection and survival rates of the compound of the present invention.
Figure 3:
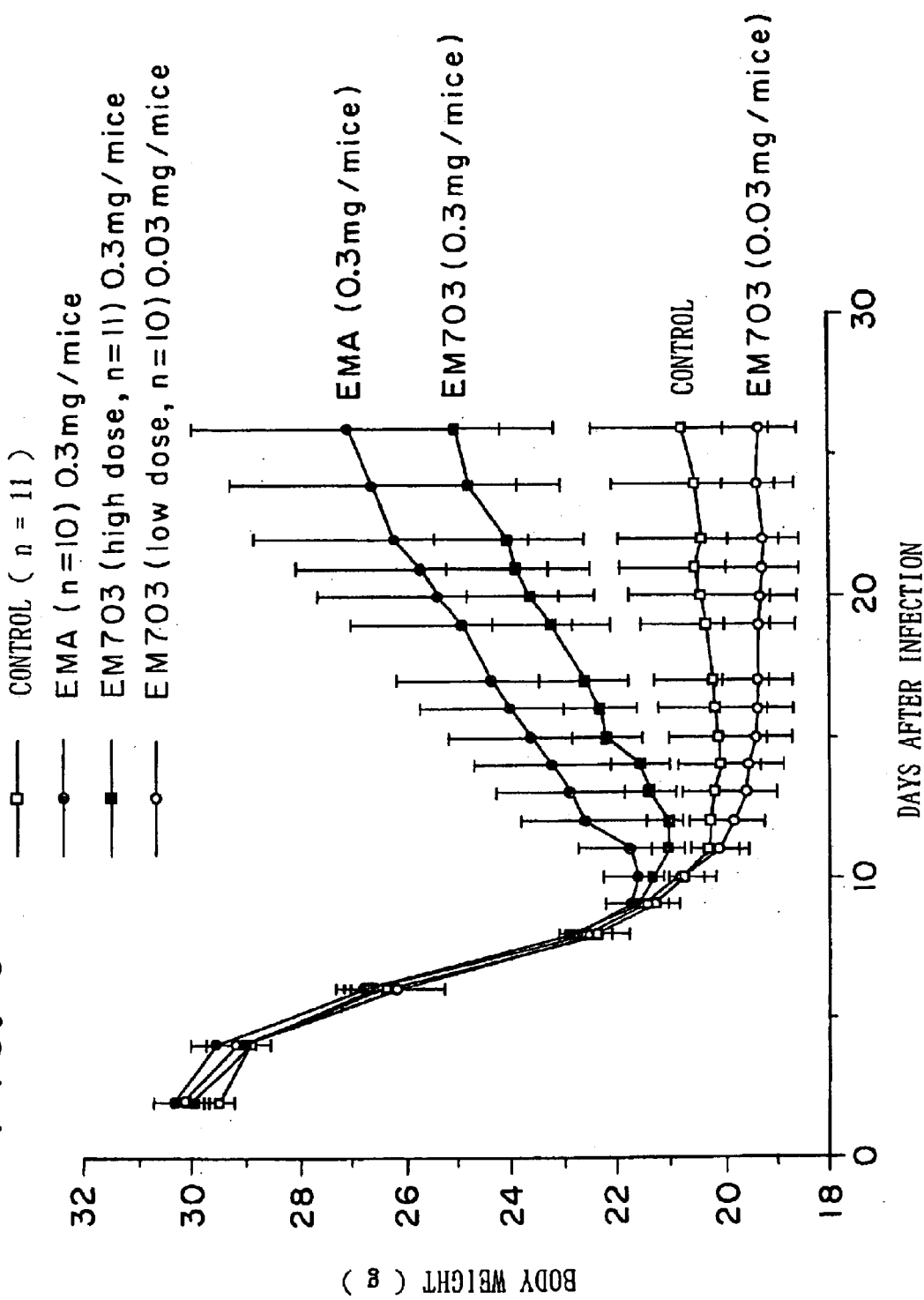
FIG. 3 is a graph showing suppressive effect of the compound of the present invention on bleomycin-induced pulmonary fibrosis.

The present invention is explained by illustrating referential examples and examples, but is not limited within these examples.

REFERENTIAL EXAMPLE 1

Synthesis of EM701

Glacial acetic acid solution of erythromycin A (12.4 g, 16.9 mmol) was stirred at room temperature for 2 hours, added slowly aqueous sodium hydrogen carbonate and neutralized. The reaction mixture was extracted with chloroform, dehydrated the organic layer with sodium sulfate, filtered off the sodium sulfate and removed the solvent by distillation to obtain crude substance. The crude substance was purified with silica gel chromatography (chloroform:methanol:aqueous ammonia= 10:0.5:0.01→10:1:0.05) to obtain EM201 (7.7 g, 63%). Subsequently, potassium carbonate (1.4 g, 10.6 mmol) was added to the methanol solution (100 ml) of EM 201 (7.6 g, 10.6 mmol) and refluxed for 2 hours. After distilled off the solvent, the residue was dissolved in aqueous sodium hydrogen carbonate and extracted with chloroform. The mixture was dehydrated with sodium sulfate, filtered and removed the sodium sulfate, then the obtained crude substance was purified by silica gel chromatography (chloroform:methanol:aqueous ammonia= 10:0.5:0.01→10:1:0.05) to obtain EM701 (5.9 g, 78%, white powder).

Example 1

Synthesis of de(3'-N-methyl)-8,9-anhydro-pseudoerythromycin A 6,9-hemiketal (EM703)

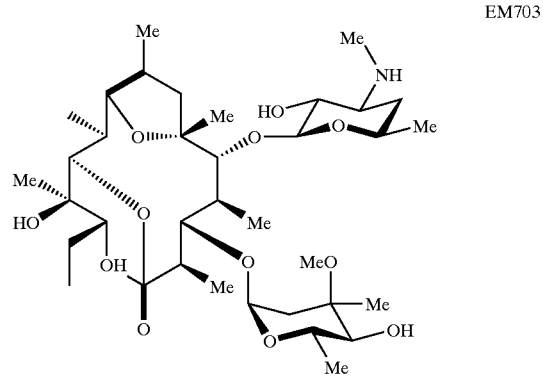

EM703

Sodium acetate (3.9 g, 48.5 mmol) and iodine (2.5 g, 9.7 mmol) were added in this order to methanol (52.0 mL)-water (13.0 mL) solution of EM701 (6.9 g, 9.7 mmol) at room temperature, and stirred at 50° C. for 3 hours. During the stirring, 1N aqueous solution of sodium hydroxide was added to maintain at pH 8–9 continuously. After confirming the completion of the reaction by TLC, the reaction mixture was diluted with aqueous ammonia (7.5 mL)-water (200 mL), and extracted with dichloromethane. After dehydrating the organic layer with sodium sulfate, the sodium sulfate was removed by filtration and distilled off the solvent to obtain crude substance. The crude substance was purified by silica gel column chromatography (chloroform:methanol:aqueous ammonia= 10:0.5:0.01→10:1:0.05) to obtain EM703 (4.8 g, Yield: 70%, white powder). EM703: m. p.: 177–180° C.

Example 1 is a known compound. This is shown at line 703 in Table 1.

Example 2

Synthesis of bis-de(3'-N-methyl)-8,9-anhydro-pseudo erythromycin A 6,9-hemiketal (EM721)

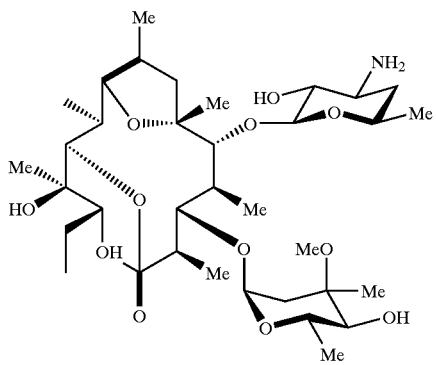

EM721

Sodium (4.5 g, 1.67 mmol) was added in methanol (15 mL) to prepare methanol solution of sodium methoxide, and EM703 (195.4 mg, 0.279 mmol) and iodine (353.6 mg, 1.393 mmol) were added in this order at 0° C. and stirred for 3 hours. After confirming completion of the reaction by TLC, sodium thiosulfate (0.8 g), aqueous ammonia (0.5 mL) and water (80 mL) were added and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM721 (166.3 mg, Yield: 87%, white powder).

EM721: m. p.: 134–136° C.

IR (KBr) v: 3467.4, 2973.7, 2935.1, 2879.2. 1700.9, 1637.3, 1457.9, 1380.8. 1265.1, 1166.7, 1126.2, 1079.9, 1037.5, 1016.3 cm$^{-1}$.

HRMS (FAB)m/z: $C_{35}H_{61}NO_{12}Na$ [M+Na]$^+$ Calculated 710.4091, Found 710.4060.

Example 3

Synthesis of bis-de(3'-N-methyl)-3'-N-ethyl-8,9-anhydro-pseudoerythromycin A 6,9-hemiketal (EM722)

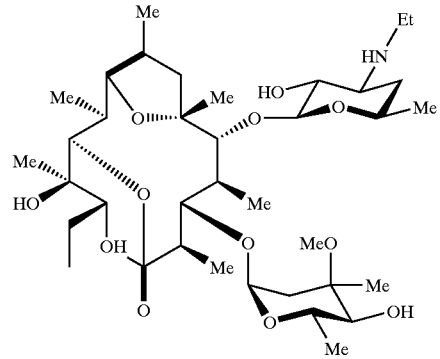

EM722

N,N-Diisopropylethylamine (26.6 μL, 0.153 mmol) and ethyl iodide (12.2 μL, 0.153 mmol) were added to dimethylformamide (1.0 mL) solution of EM721 (21.0 mg, 0.0305 mmol) and stirred at room temperature for 4 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM722 (7.0 mg, Yield: 32%, white powder).

EM722: m. p.: 124–126° C.

IR (KBr) v: 3471.6, 2933.2, 1704.8, 1457.9, 1378.9, 1263.1, 1166.7, 1128.2, 1074,2, 1037.5, 1018.2 cm$^{-1}$.

HRMS (FAB)m/z: $C_{37}H_{65}NO_{12}Na$ [M+Na]$^+$ Calculated 738.4404 Found 738.4393.

Example 4

Synthesis of bis-de(3'-N-methyl)-3',3'-N,N-diethyl-8,9-anhydro-pseudoerythromycin A 6,9-hemiketal (EM723)

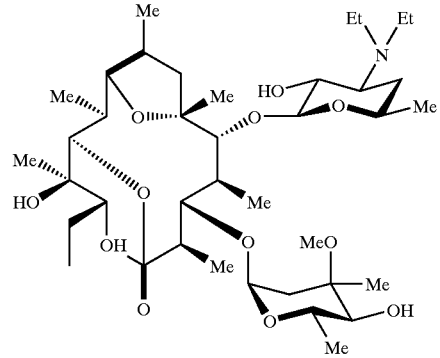

EM723

N,N-Diisopropylethylamine (26.6 μL, 0.153 mmol) and ethyl iodide (12.2 μL, 0.153 mmol) were added to dimethylformamide (1.0 mL) solution of EM721 (21.0 mg, 0.0305 mmol) and stirred at room temperature for 4 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM723 (10.3 mg, Yield: 45%, white powder).

EM723: m. p.: 165–168° C.

IR (KBr) v: 3473.7, 2935.1, 1699.0, 1382.7, 1317.1, 1267.0, 1166.7, 1126.2, 1108,9, 1078.0, 1016.3 $c^{-1}$.

HRMS (FAB)m/z: $C_{39}H_{69}NO12Na$ $[M+Na]^+$ Calculated 766.4717 Found 766.4710.

Example 5

Synthesis of bis-de(3'-N-methyl)-3'-N-allyl-8,9-anhydro-pseudoerythromycin A 6,9-hemiketal (EM724)

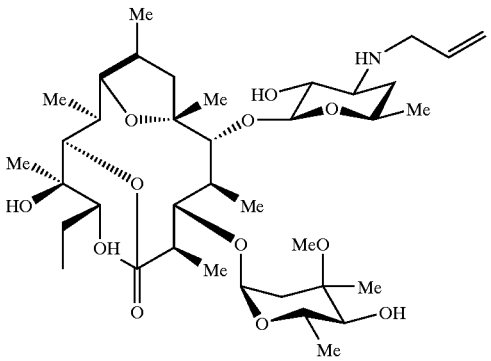

EM724

Allyl bromide (148.3 µL, 1.714 mmol) was added to dichloromethane (5.7 mL) solution of EM721 (117.8 mg, 0.171 mmol) and N,N-Diisopropylethylamine (298.6 µL, 1.714 mmol) at 0° C. and stirred at room temperature for 2 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM724 (21.9 mg, Yield: 30%, white powder) was obtained.

EM724: m. p.: 106–109° C.

IR (KBr) v: 3448.8, 2971.8, 2933.2, 1718.3, 1637.3, 1380.8, 1265.1, 1166.7, 1126,2, 1078.0, 1037.5, 1016.3 $cm^{-1}$.

HRMS (FAB)m/z: $C_{38}H_{65}NO_{12}Na$ $[M+Na]^+$ Calculated 750.4404, Found 750.4420.

Example 6

Synthesis of bis-de(3'-N-methyl)-3',3'-N,N-diallyl-8,9-anhydro-pseudoerythromycin A 6,9-hemiketal (EM725)

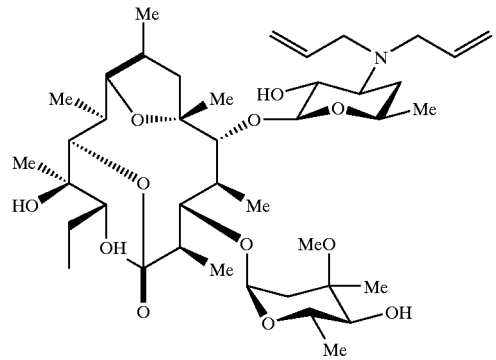

EM725

Allyl bromide (148.3 µL, 1.714 mmol) was added to dichloromethane (5.7 mL) solution of EM721 (117.8 mg, 0.171 mmol) and N,N-Diisopropylethylamine (298.6 µL, 1.714 mmol) at 0° C., stirred at room temperature for 2 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM725 (64.3 mg, Yield: 59%, white powder).

EM725: m. p.: 140–142° C.

IR (KBr) v: 3471.7, 2971.8, 2927.4, 1700.9, 1637.3, 1380.8, 1317.1, 1265.1, 1166.7, 1124.3, 1114.7, 1049.1, 1016.3 $cm^{-1}$.

HRMS (FAB)m/z: $C_{41}H_{69}NO_{12}Na$ $[M+Na]^+$ Calculated 790.4717 Found 790.4716.

Example 7

Synthesis of bis-de(3'-N-methyl)-3'-N-acetyl-8,9-anhydro-pseudoerythromycin A 6,9-hemiketal (EM726)

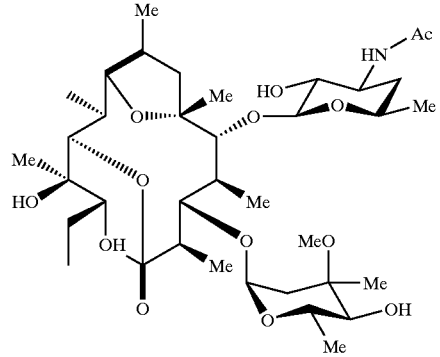

EM726

Acetic anhydride (8.4 µL, 0.0759 mmol) was added to dichloromethane (1.6 mL) solution of EM721 (34.8 mg, 0.0506 mmol) at 0° C., stirred for 10 minutes and further stirred at room temperature for 30 minutes. After confirming completion of the reaction by TLC, the reaction mixture was diluted with water and extracted with dichloromethane. The organic layer was dehydrated by adding sodium sulfate filtered to remove the sodium sulfate, and removed the solvent to obtain crude substance. The crude substance was purified by silica gel column chromatography (chloroform: methanol=100:1→20:1) to obtain EM726 (33.4 mg, Yield: 91%, white powder).

EM726: m. p.: 137–139° C.

IR (KBr) v: 3417.2, 2973.7, 2935.1, 1699.0, 1454.1, 1376.9, 1317.1, 1268.9, 1166.7, 1124.3, 1076.1, 1033.7, 1018.2, 1000.9 cm$^{-1}$.

HRMS (FAB)m/z: $C_{37}H_{63}NO_{13}Na$ [M+Na]$^+$ Calculated 752.4197 Found 752.4202.

Example 8

Synthesis of de(3'-N-methyl)-3'-N-sulfonyl-8,9-anhydro-pseudoerythromycin A 6,9-hemiketal (EM727)

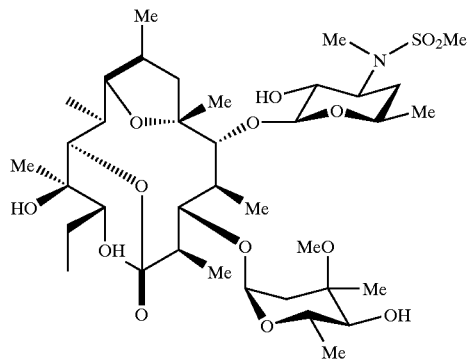

EM727

Methanesulfonyl chloride (9.3 μL, 0.249 mmol) was added to dichloromethane (4.2 ml) solution of EM703 (87.6 mg, 0.125 mmol) at 0° C. and stirred for 3 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol=100:1→20:1) to obtain EM727 (37.2 mg, Yield: 91%, white powder).

EM727: m. p.: 225–228° C.

IR (KBr) v: 3497.6, 2973.7, 2935.1, 1704.8, 1463.7, 1380.8, 1326.8, 1319.1, 1265.1, 1166.7, 1141.7, 1074.2, 1041.4, 1016.3 cm$^{-1}$.

HRMS (FAB)m/z: $C_{37}H_{65}NO_{14}SNa$ [M+Na]$^+$ Calculated 802.4023 Found 802.3995.

Example 9

Synthesis of bis-de(3'-N-methyl)-3'-N-propargyl-8,9-anhydro-pseudoerythromycin A 6,9-hemiketal (EM728)

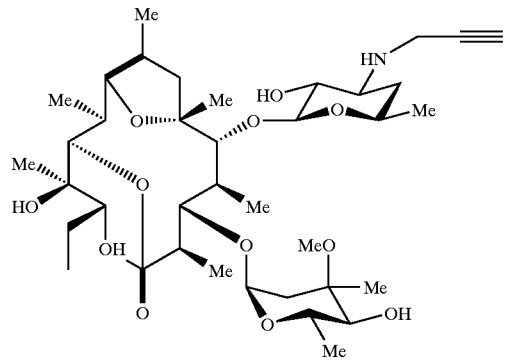

EM728

3-Bromopropine (137.8 μL, 1.546 mmol) was added to dichloromethane (5.2 mL) solution of EM721 (106.3 mg, 0.155 mmol) and N,N-Diisopropylethylamine (269.3 μL, 1.546 mmol), and stirred at room temperature for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM728 (41.3 mg, Yield: 37%, white powder).

EM728: m. p.: 113–115° C.

IR (KBr) v: 3413.0, 2973.7, 2935.1, 1706.8, 1457.9, 1382.7, 1263.1, 1166.7, 1126.2, 1078.0, 1039.4, 1016.5 cm$^{-1}$.

HRMS (FAB)m/z: $C_{38}H_{63}NO_{12}Na$ [M+Na]$^+$ Calculated 748.4248 Found 748.4260.

Example 10

Synthesis of bis-de(3'-N-methyl)-3',3'-N,N-dipropargyl-8, 9-anhydro-pseudoerythromycin A 6,9-hemiketal (EM729)

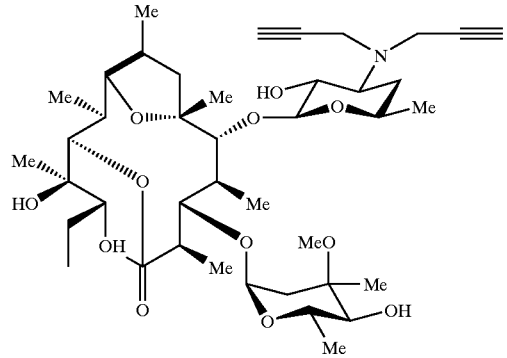

EM729

3-Bromopropine (137.8 μL, 1.546 mmol) was added to dichloromethane (5.2 mL) solution of EM721 (106.3 mg, 0.155 mmol) and N,N-Diisopropylethylamine (269.3 μL, 1.546 mmol) and stirred at room temperature for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01→10:1:0.05) to obtain EM729 (27.9 mg, Yield: 24%, white powder).

EM729: m. p.: 123–125° C.

IR (KBr) v: 3415.0, 3309.2, 2971.8, 2933.2, 2877.3, 1706.7, 1457.9, 1375.0, 1263.1, 1166.7, 1116.6, 1072.2, 1049.1, 1035.6, 1016.3 cm$^{-1}$.

HRMS (FAB)m/z: $C_{41}H_{65}NO_{12}Na$ [M+Na]$^+$ Calculated 786.4404 Found 786.4404.

Example 11

Synthesis of bis-de(3'-N-methyl)-3'-N-propyl-8,9-anhydro-pseudoerythromycin A 6,9-hemiketal (EM730)

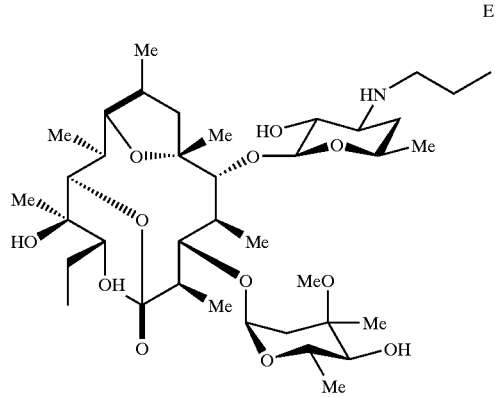

N,N-Diisoproplylethylamine (59.6 μL, 0.342 mmol) and 1-iodopropane (33.3 μL, 0.342 mmol) were added in this order to acetinitrile (2.3 mL) solution of EM721 (23.5 mg, 0.0342 mmol) and refluxed at 80° C. for 20 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM730 (5.7 mg, Yield: 23%, white powder).

EM730: m. p.: 109–111° C.

IR (KBr) v: 3435.0, 2971.8, 2935.1, 2879.2, 1706.7, 1459.8, 1380.8, 1263.1, 1166.7, 1126.2, 1078.0, 1035.6, 1016.3 cm$^{-1}$.

HRMS (FAB)m/z: $C_{38}H_{67}NO_{12}Na$ [M+Na]$^+$ Calculated 752.4560 Found 752.4564.

Example 12

Synthesis of bis-de(3'-N-methyl)-3',3'-N,N-di-propyl-8,9anhydro-pseudoerythromycin A 6,9-hemiketal (EM731)

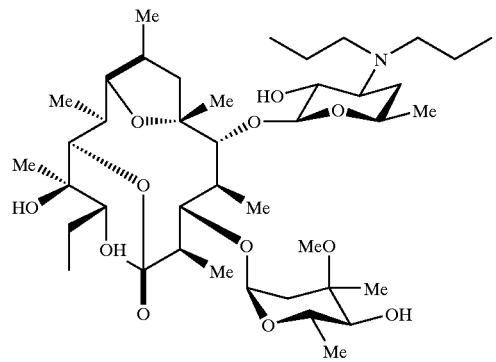

N,N-Diisopropylethylamine (59.6 μL. 0.342 mmol) and 1-iodopropane (33.3 μL, 0.342 mmol) were added in this order to acetinitrile (2.3 mL) solution of EM721 (23.5 mg, 0.0342 mmol) and refluxed at 80° C. for 20 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM731 (12.0 mg, Yield: 40%, white powder).

EM731: m. p.: 148–151° C.

IR (KBr) v: 3435.0, 2964.1, 2933.2, 2873.4, 1706.7, 1457.9, 1376.9, 1319.1, 1263.1, 1166.7, 1110.8, 1081.9, 1049.1, 1035.6, 1016.3 cm$^{-1}$.

HRMS (FAB)m/z: $C_{41}H_{73}NO_{12}Na$ [M+Na]$^+$ Calculated 794.5030 Found 794.5005.

Example 13

Synthesis of bis-de(3'-N-methyl)-3'-N-benzyl-8,9-anhydro-pseudoerythromycin A 6,9-hemiketal (EM732)

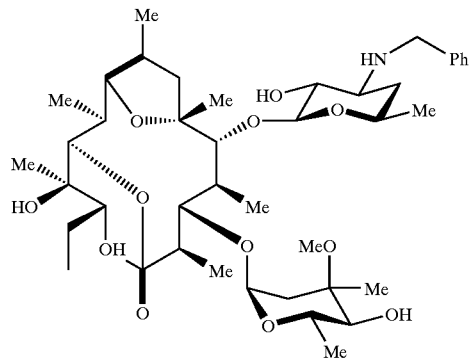

Benzyl chloride (297.3 μL, 2.584 mnol) was added to dichloromethane (4.3 mL) solution of EM721 (88.8 mg, 0.129 mmol) and N,N-diisopropylethylamine (450.1 μL, 2.584 mmol) at room temperature and stirred for 96 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 15:1:0.1) to obtain EM732 (49.9 mg, Yield: 50%, white powder).

EM732: m. p.: 126–128° C.

IR (KBr) v: 3410.0, 2971.8, 2935.1, 1706.7, 1456.0, 1378.9, 1263.1, 1166.7, 1124.3, 1078.0, 1049.1, 1039.4, 1016.3, 983.5, 937.2, 808.0, 752.1 $cm^{-1}$.

HRMS (FAB)m/z: $C_{42}H_{67}N_{12}Na$ $[M+Na]^+$ Calculated 800.4560 Found 800.4565.

Example 14

Synthesis of bis-de(3'-N-methyl)-3',3'-N,N-di-benzyl-8,9-anhydro-pseudoerythromycin A 6,9-hemiketal (EM733)

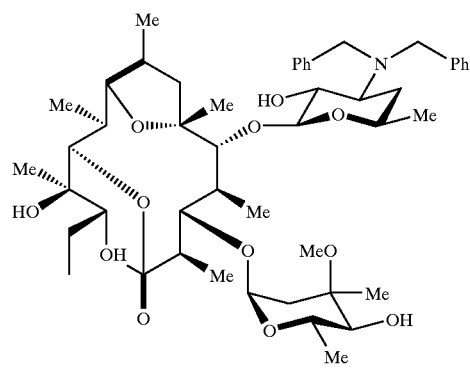

EM733

N,N-Diisopropylethylamine (135.9 μL, 0.780 mmol) and benzyl chloride (89.7 μL, 0.780 mmol) were added in this order to acetinitrile (1.3 mL) solution of EM721 (26.8 mg, 0.0390 mmol) and refluxed at 80° C. for 60 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM733 (19.6 mg, Yield: 58%, white powder).

EM733: m. p.: 149–152° C.

IR (KBr) v: 3420.6, 2969.8, 2935.1, 1700.9, 1454.1, 1375.0, 1324.9, 1263.1, 1166.7, 1116.6, 1076.1, 1049.1, 1016.3, 752.1, 700.0 $cm^{-1}$.

HRMS (FAB)m/z: $C_{49}H_{73}NO_{12}Na$ $[M+Na]^+$ Calculated 890.5030 Found 890.5032

Example 15

Synthesis of de(3'-dimethylamino)-3'-piperidino-8,9-anhydro-pseudoerythromycin A 6,9-hemiketal (EM734)

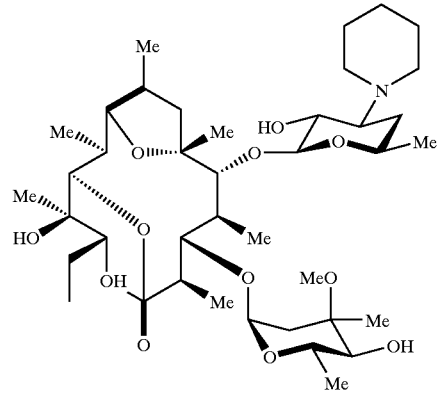

EM734

N,N-Diisopropylethylamine (42.5 μL, 0.244 mmol) and 1,5-dibromopentane (33.2 μL, 0.244 mmol) were added in this order to acetinitrile (4.9 mL) solution of EM721 (16.8 mg,0.0244 mmol) and refluxed at 80° C. for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM734 (13.3 mg, Yield: 72%, white powder).

EM734: m. p.: 128–130° C.

IR (KBr) v: 3420.0, 2971.8, 2935.1, 2858.0, 1710.6, 1454.1, 1380.8, 1319.1, 1263.1, 1164.8, 1110.8, 1074.2, 1047.2, 1016.3 $cm^{-1}$.

HRMS (FAB)m/z: $C_{40}H_{70}NO_{12}[M+Na]^+$ Calculated 756.4897 Found 756.4901

Example 16

Synthesis of de(3'-dimethylamino)-3'-pyrrolidino-8,9-anhydro-pseudoerythromycin A 6,9-hemiketal (EM735)

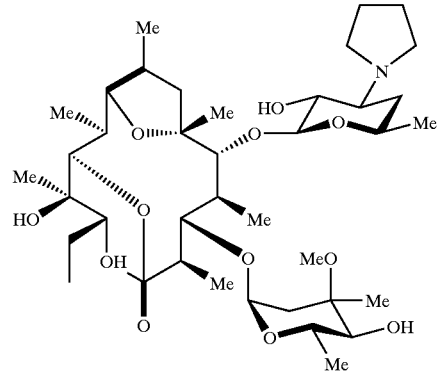

EM735

N,N-diisopropylethylamine (40.2 μL, 0.231 mmol) and 1,4-dibromobutane (27.6 μL, 0.231 mmol) were added in this order to acetinitrile (4.6 mL) solution of EM721 (15.9 mg, 0.0231 mmol) and refluxed at 80° C. for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=10:1:0.1) to obtain EM735 (11.9 mg, Yield: 70%, white powder).

EM735: m. p.: 127–129° C.

IR (KBr) v: 3420.0, 2971.8, 2937.1, 1702.8, 1457.9, 1382.7, 1265.1, 1166.7, 1124.3, 10761.1, 1049.1, 1016.3 cm$^{-1}$.

HRMS (FAB)m/z: $C_{39}H_{68}N_{12}$ [M+Na]$^+$ Calculated 742.4741 Found 742.4743

Example 17

Synthesis of bis-de(3'-N-methyl)-3'-N-(2-propyl)-8,9-anhydro-pseudoerythromycin A 6,9-hemiketal (EM736)

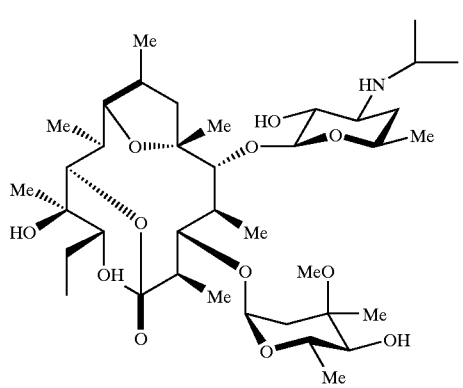

EM736

N,N-Diisopropylethylamine (459.2 μL, 2.636 mmol) and 2-bromopropane (247.5 μL, 2.636 mmol) were added in this order to acetinitrile (4.4 mL) solution of EM721 (90.6 mg, 0.132 mmol) and stirred at 80° C. for 72 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=10:1:0.1) to obtain EM736 (25.3 mg, Yield: 26%, white powder). The raw material EM721 was recovered 47.1 mg (Yield: 52%).

EM736: m. p.: 102–104° C.

IR (KBr) v: 3420.0, 2971.8, 2933.2, 2877.3, 1718.3, 1459.8, 1380.8, 1263.1, 1166.7, 1126.2, 1078.0, 1049.1, 1016.3 cm$^{-1}$.

HRMS (FAB)m/z: $C_{38}H_{67}NO_{12}Na$ [M+Na]$^+$ Calculated 752.4560 Found 752.4576.

Example 17 is a known compound. This is shown at line 736 in Table 1.

Example 18

Synthesis of de(3-O-cladinosyl)-8,9-anhydro-pseudo erythromycin A 6,9-hemiketal (EM737)

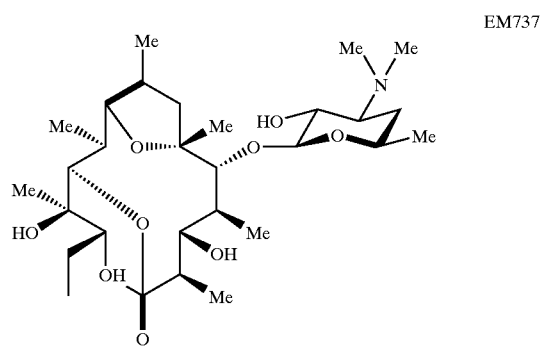

EM737 p-toluenesulfonic acid monohydrate (80.3 μL, 0.422 mmol) was added to dimethylformamide (5.6 mL) solution of EM701 (201.6 mg, 0.282 mmol) and stirred at 50° C. for 8 hours. After confirming completion of the reaction by TLC, the reaction mixture was diluted with water, adjusted to pH 8.0 by adding saturated aqueous sodium hydrogen carbonate and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM737 (84.7 mg, Yield: 54%, white powder).

EM737: m. p.: 109–111° C.

IR (KBr) v: 3486.7, 2973.7, 2937.1, 2877.3, 1708.6, 1631.5, 1457.9, 1382.7, 1265.1, 1164.8, 1110.8, 1076.1, 1039.4 cm$^{-1}$.

HRMS (FAB)m/z: $C_{29}H_{52}N_9$ [M+Na]$^+$ Calculated 558.3641 Found 558.3616

Example 19

Synthesis of bis-de(3'-N-methyl)-3'-N-hexyl-8,9-anhydro-pseudoerythromycin A 6,9-hemiketal (EM738)

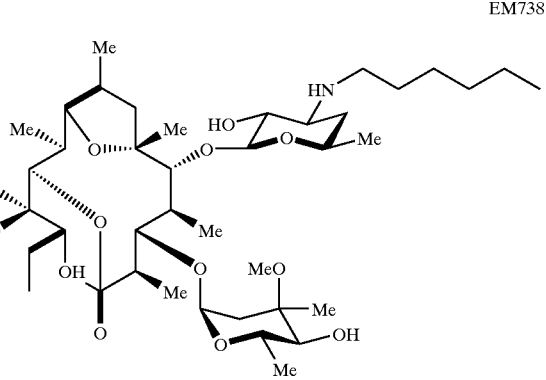

EM738

N,N-Diisopropylethylamine (408.5 μL, 2.345 mmol) and 1-bromohexane (328.7 μL, 2.345 mmol) were added in this order to acetinitrile (3.9 mL) solution of EM721 (80.6 mg, 0.117 mmol) and stirred at 60° C. for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia 15:1:0.1) to obtain EM738 (33.7 mg, Yield: 45%, white powder). The raw material EM721 was recovered 24.6 mg (Yield: 31%).

EM738: m. p.: 115–118° C.

IR (KBr) ν: 3430.3, 2969.8, 2933.2, 2858.0, 1712.5, 1459.8, 1378.9, 1317.1, 1263.1, 1166.7, 1126.2, 1078.0, 1047.2, 1039.4, 1016.3 cm$^{-1}$.

HRMS (FAB)m/z: $C_{41}H_{74}NO_{12}$ [M+Na]$^+$ Calculated 772.5210 Found 772.5214.

Example 20

Synthesis of bis-de(3'-N-methyl)-3',3'-N,N-dihexyl-8,9-anhydro-pseudoerythromycin A 6,9-hemiketal (EM739)

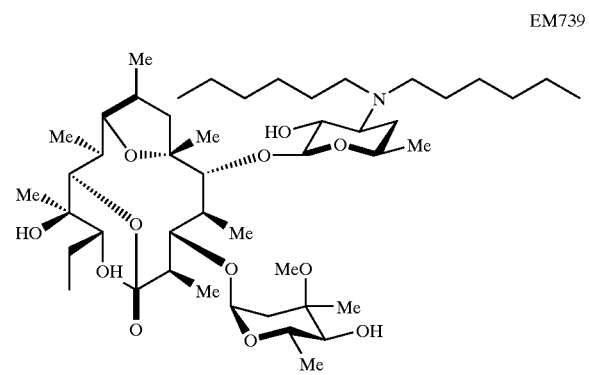

EM739

N,N-Diisopropylethylamine (116.0 μL, 0.666 mmol) and 1-bromohexane (93.6 μL, 0.666 mmol) were added in this order to acetinitrile (1.1 mL) solution of EM721 (22.9 mg, 0.0333 mmol) and stirred at 60° C. for 72 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM739 (20.1 mg, Yield: 71%, white powder).

EM739: m. p.: 158–160° C.

IR (KBr) ν: 3490.0, 2958.3, 2931.3, 2871.5, 2858.0, 1702.8, 1459.8, 1376.9, 1319.1, 1265.1, 1166.7, 1126.2, 1083.8, 1016.3 cm$^{-1}$.

HRMS (FAB)m/z: $C_{47}H_{86}NO_{12}$ [M+H]$^+$ Calculated 856.6149 Found 856.6132.

Example 21

Synthesis of bis-de(3'-N-methyl)-3'-N-(2-fluoroethyl)-8,9-anhydro-pseudoerythromycin A 6,9-hemiketal (EM740)

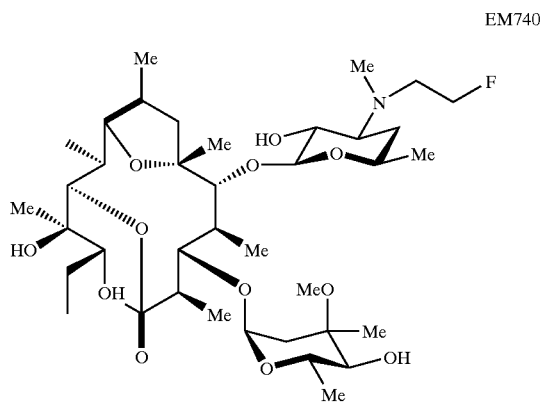

EM740

N,N-Diisopropylethylamine (347.7 μL, 1.996 mmol) and 1-bromo-2-fluoroethane (148.6 μL, 1.996 mmol) were added to dimethylformamide (3.3 mL) solution of EM703 (70.0 mg, 0.0998 mmol) at room temperature and stirred for 48 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 20:1:0.1) to obtain EM740 (36.0 mg, Yield: 48%, white powder). The raw material EM703 was recovered 25.5 mg (Yield: 36%).

EM740: m. p.: 138–140° C.

IR (KBr) ν: 3480.8, 2973.7, 2937.1, 2879.2, 1704.8, 1457.9, 1376.9, 1319.1, 1265.1, 1166.7, 1126.2, 1114.7, 1076.1, 1049.1, 1035.6, 1016.3 cm$^{-1}$.

HRMS (FAB)m/z: $C_{38}H_{66}NO_{12}Fna$ [M+Na]$^+$ Calculated 770.4467 Found 770.4469.

Example 22

Synthesis of de(3'-N-methyl)-3'-cyanomethyl-8,9-anhydro-pseudoerythromycin A 6,9-hemiketal (EM742)

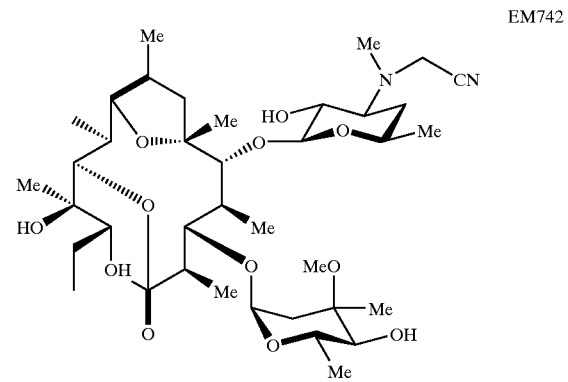

EM742

N,N-Diisopropylethylamine (326.9 μL, 1.847 mmol) and bromoacetinitrile (128.3 μL, 1.847 mmol) were added to dimethylformamide (3.1 mL) solution of EM703 (64.6 mg, 0.0921 mmol) at room temperature and stirred for 4 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 20:1:0.1) to obtain EM742 (53.1 mg, Yield: 78%, white powder).

EM742: m. p.: 110–112° C.

IR (KBr) v: 3485.5, 2973.7, 2935.1, 2863.8, 1702.8, 1456.0, 1382.7, 1319.1, 1265.1, 1166.7, 1126.2, 1074.2, 1037.5, 1016.3 cm$^{-1}$.

HRMS (FAB)m/z: $C_{38}H_{64}NO_{12}Na[M+Na]^+$ Calculated 763.4356 Found 763.4377.

REFERENTIAL EXAMPLE 2

Synthesis of de(12-hydroxy)-de[12-(1-hydroxypropyl)]-12-oxo-8,9-anhydro-pseudoerythromycin A 6,9-hemiketal (EM705)

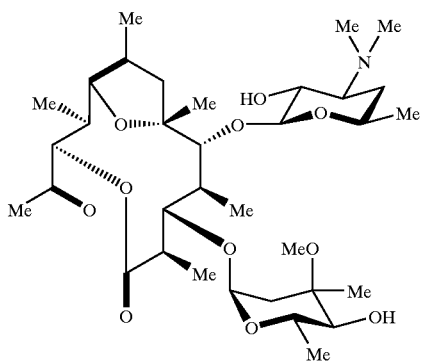

Lead tetra acetate (508.0 mg, 1.136 mmol) was added to dichloromethane (24.0 ml) solution of EM701 (508.0 mg, 0.701 mmol) and stirred at room temperature for 40 minutes. After confirming completion of the reaction by TLC, the reaction mixture was diluted with saturated brine-aqueous saturated sodium hydrogencarbonate (1:1, v/v) and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 10:0.5:0.01) to obtain EM705 (282.7 mg, Yield: 61%, white powder).

EM705: m. p.: 108–112° C.

IR (KBr) v: 3488, 2972, 2883, 1740, 1724, 1458, 1379, 1244, 1165, 1107, 1093, 1076, 1055, 1034, 1016 cm$^{-1}$.

HRMS (FAB): $C_{34}H_{58}NO_{11}[M+H]^+$ Calculated 656.4010 Found 656.4021.

Example 23

Synthesis of de(12-hydroxy)-de[12-(1-hydroxypropyl)]-12-hydroxyoxime-8,9-anhydro-pseudoerythromycin A 6,9-hemiketal (EM743) and the salt thereof

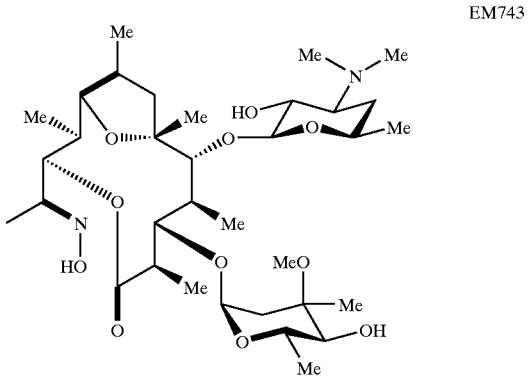

Pyridine (0.9 mL) was slowly added at 0° C. to ethanol (0.9 mL) solution of EM705 (116.5 mg, 0.1781 mmol) and hydroxylamine hydrochloride (32.0 mg, 0.533 mmol) and stirred for 3 hours. After confirming completion of the reaction by TLC, the reaction mixture was diluted with water and extracted with dichloromethane. The organic layer was dehydrated by adding sodium sulfate. filtered to remove the sodium sulfate, and removed the solvent to obtain crude substance. The crude substance was purified by silica gel column chromatography (chloroform:methanol:aqueous ammonia=10:0.5:0.01→10:1:0.05) to obtain EM743 (114.5 mg, Yield: 96%, white powder).

EM743: m. p.: 141–143° C.

IR (KBr) v: 3485.8, 2971.8, 2937.1, 2883.1, 1737.5, 1459.8, 1378.9, 1255.4, 1247.7, 1166.7, 1112.7, 1089.6, 1076.1, 1037.5, 1014.4 cm$^-$.

HRMS (FAB)m/z: $C_{34}H_{59}NO_{11}[M+H]^+$ Calculated 671.4112 Found 671.4108.

Example 24

Synthesis of de[(3'-N-methyl)-[3'-N-(3-hydroxy-1-propyl)]-8,9-anhydro-pseudoerythromycin A 6,9-hemiketal (EM744)

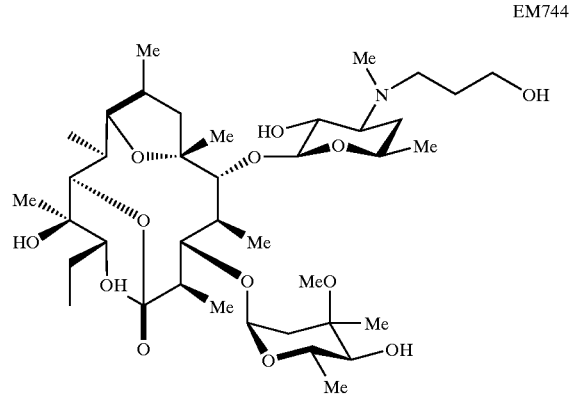

N,N-Diisopropylethylamine (338.3 μL, 1.942 mmol) and 3-bromo-1-propanol (175.6 μL, 1.942 mmol) were added to dimethylformamide (3.3 mL) solution of EM703 (68.1 mg, 0.0971 mmol) at room temperature and stirred for 48 hours. After confirming completion of there action by TLC, there action mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 15:1:0.1)to obtain EM744(27.7 mg,Yield: 38%, white powder). The raw material EM703 was recovered 22.5 mg (Yield: 33%).

EM744: m. p.: 142–145° C.

IR (KBr) v: 3478.8, 2973.7, 2937.1, 2877.3, 1700.9, 1635.3, 1459.8, 1403.9, 1382.7, 1317.1, 1267.0, 1166.7, 1126.2, 1114.7, 1076.1, 1049.1, 1035.6, 1016.3 cm$^{-1}$.

HRMS (FAB)m/z: $C_{39}H_{69}NO_{13}Na$ $[M+Na]^+$ Calculated 782.4666 Found 782.4667.

Example 25

Synthesis of de(3'-N-methyl)-3'-N-(2-acetoxyethyl)-8,9-anhydro-pseudoerythromycin A 6,9-hemiketal (EM745)

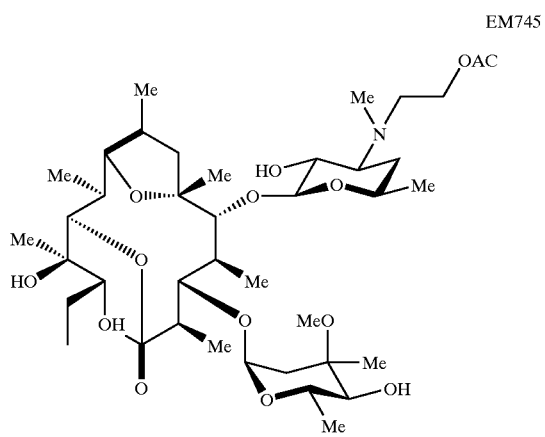

EM745

N,N-Diisopropylethylamine (106.8 μL, 0.613 mmol) and 2-bromoethylacetate (67.6 μL, 0.613 mmol) were added to dimethylacetamide (1.0 mL) solution of EM703 (21.5 mg, 0.0307 mmol) at room temperature and stirred for 48 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia= 20:1:0.1) to obtain EM745 (6.0 mg, Yield: 25%, white powder).

EM745: m. p.: 131–133° C.

IR (KBr) v: 3500.2, 3477.0, 2973.7, 2937.1, 2877.3, 1735.6, 1700.9, 1457.9, 1376.9, 1319.1, 1265.1, 1166.7, 1126.2, 1078.0, 1037.5, 1016.3 cm$^{-1}$.

HRMS (FAB)m/z: $C_{40}H_{69}NO_{14}Na$ $[M+Na]^+$ Calculated 810.4615 Found 810.4629

Example 26

Synthesis of de[12-(hydroxypropyl)]-8,9-anhydro-pseudo erythromycin A 6,9-hemiketal (EM746)

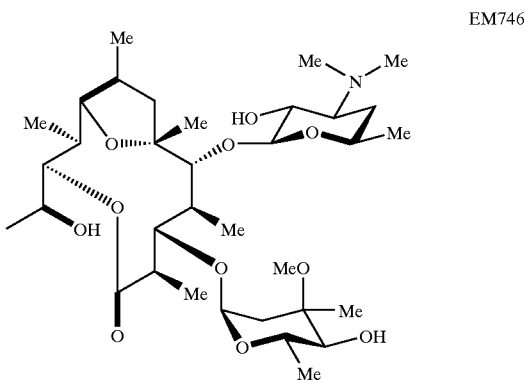

EM746

Sodium borohydride (21.8 mg, 0.575 mmol) was added to methanol (2.9 mL) solution of EM705 (37.7 mg, 0.0575 mmol) at −78° C. and stirred for 30 minutes. Temperature of the reaction mixture was increased to 0° C. and further stirred for 30 minutes. After confirming completion of the reaction by TLC, the reaction was terminated by adding acetone (0.5 ml). The reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM746 (35.8 mg, Yield: 95%, white powder).

EM746: m. p.: 116–118° C.

IR (KBr) v: 3457.7, 2971.3, 2939.0, 1731.8, 1631.5, 1457.9, 1378.9, 1265.1, 1166.7, 1110.8, 1078.0, 1041.4, 1016.3 cm$^{-1}$.

HRMS (FAB)m/z: $C_{34}H_{59}NO_{11}Na$ $[M+Na]^+$ Calculated 680.3963 Found 680.3963

Example 27

Synthesis of de(3'-dimethylamino)-3'-morpholino-8,9-anhydro-pseudoerythromycin A 6,9-hemiketal (EM747)

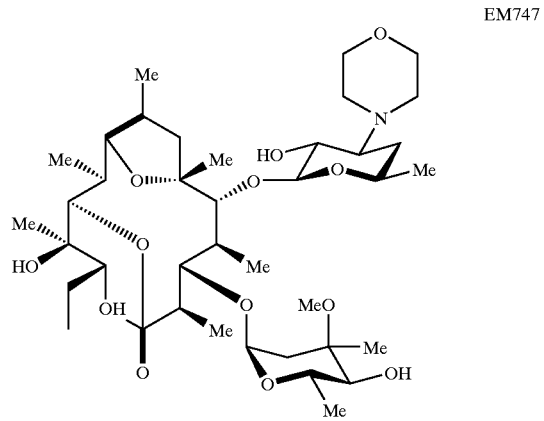

EM747

N,N-Diisopropylethylamine (45.8 μL, 0,263 mmol) and bis(2-bromoethyl) ether (33.1 μL, 0.263 mmol) were added in this order to acetonitrile (2.6 mL) solution of EM721 (18.1 mg, 0.0263 mmol) and stirred at 80° C. for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM747 (12.0 mg, Yield: 60%, white powder).

EM747: m. p.: 139–142° C.

IR (KBr) v: 3452.0, 2971.8, 2937.1, 2865.7, 1700.9, 1646.9, 1457.9, 1380.8, 1319.1, 1265.1, 1166.7, 1110.8, 1072.2, 1049.1, 1016.3 cm$^{-1}$.

HRMS (FAB)m/z: $C_{39}H_{67}NO_{13}Na$ [M+Na]$^+$ Calculated 780.4510 Found 780.4529

Example 28

Synthesis of de(3'-dimethylamino)-3'-[hexahydro-1 (1H)-azepinyl]-8,9-anhydro-pseudoerythromycin A 6,9-hemiketal (EM748)

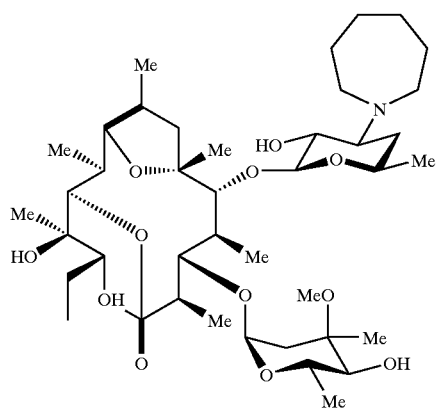

N,N-Diisopropylethylamine (49.5 µL, 0,284 mmol) and 1,6-dibromohexane (43.6 µL, 0.284 mmol) were added in this order to acetonitrile (2.8 ml) solution of EM721 (19.5 mg, 0.0284 mmol) and stirred at 80° C. for 24 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM748 (11.7 mg, Yield: 54%, white powder).

EM748: m. p.: 120–123° C.

IR (KBr) v: 3430.7, 2971.8, 2933.2, 2858.0, 1708.6, 1629.6, 1457.9, 1378.9, 1319.1, 1263.1, 1166.7, 1112.7, 1083.8, 1047.2, 1016.3 cm$^{-1}$.

HRMS (FAB)m/z: $C_{41}H_{72}NO_{12}$ [M+H]$^+$ Calculated 770.5054 Found 770.5062.

Example 29

Synthesis of bis-de(3'-N-methyl)-3',3'-N,N-di-(10-bromo-1-decanyl)-8,9-anhydro-pseudoerythromycin A 6,9-hemiketal (EM749)

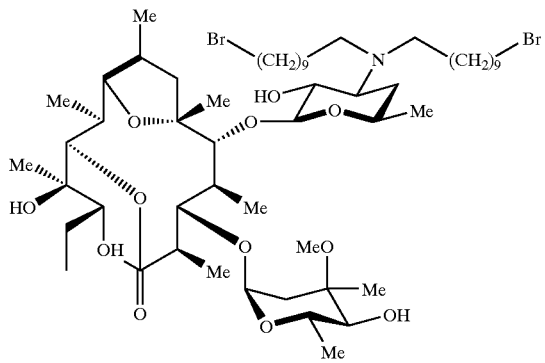

N,N-Diisopropylethylamine (45.6 µL, 0,262 mmol) and 1,10-dibromodecane(58.9 µL,0.262 mmol)were added in this order to acetonitrile (2.6 mL) solution of EM721 (18.0 mg, 0.0262 mmol) and refluxed at 80° C. for 36 hours. After confirming completion of the reaction by TLC, the reaction mixture was diluted with water and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=20:1:0.1) to obtain EM749 (14.9 mg, Yield: 51%, white powder).

EM749: m. p.: 132–134° C.

IR (KBr) v: 3448.1, 2929.3, 1700.9, 1629.6, 1459.8, 1375.0, 1319.1, 1267.0, 1166.7, 1126.2, 1081.9, 1049.1, 1016.3 cm$^{-1}$.

HRMS (FAB)m/z: $C_{55}H_{100}NO_{12}Br_2$ [M+H]$^+$ Calculated 1126 Found 1126.

Example 30

Synthesis of de(12-hydroxy)-de[12-(hydroxypropyl)]-12-amino-8,9-anhydro-pseudoerythromycin A 6,9-hemiketal (EM750)

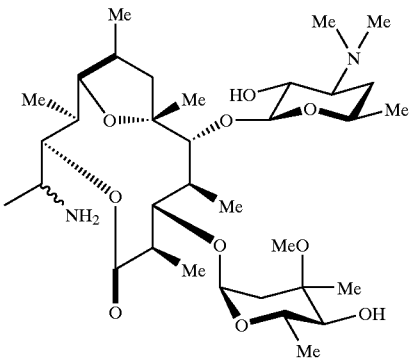

Molybdenum oxide (IV) (10.0 mg, 0,0694 mmol) and sodium borohydride (10.5 mg, 0.277 mmol) were added to ethanol (2.3 mL) solution of EM743 (15.5 mg, 0.0231 mmol) at 0° C. and stirred for 4 hours. After confirming completion of the reaction by TLC, the reaction was terminated by adding acetone (0.5 mL), and the reaction mixture was diluted with saturated brine-aqueous saturated sodium hydrogen carbonate (1:1, v/v) and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=10:1:0.1) to obtain EM750 (13.4 mg, Yield: 88%, white powder).

EM750: m. p.: 104–107° C.

IR (KBr) v: 3448.1, 2971.8, 2935.1, 1729.8, 1629.6, 1457.9, 1378.9, 1259.3, 1166.7, 1114.7, 1078.0, 1039.4, 1016.3 $cm^{-1}$.

HRMS (FAB)m/z: $C_{34}H_{60}N_2O_{10}Na$ $[M+Na]^+$ Calculated 679.4145 Found 679.4117.

REFERENTIAL EXAMPLE 3

Synthesis of de(3'-N-methyl)-de(12-hydroxy)-de-[12-(1-hydroxy propyl)]-12-oxo-8,9-anhydro-pseudoerythromycin A 6,9-hemiketal (EM706)

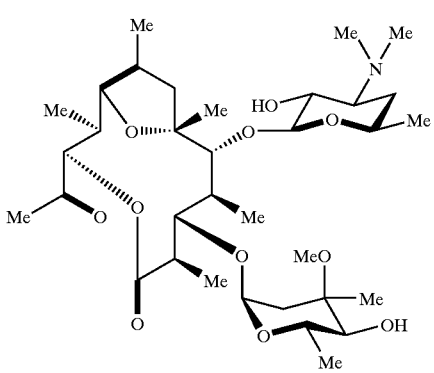

EM706

Lead tetra acetate (508.0 mg, 1.136 mmol) was added to dichloromethane (24.0 ml) solution of EM701 (508.0 mg, 0.701 mmol) and stirred at room temperature for 40 minutes. After confirming completion of the reaction by TLC, the reaction mixture was diluted with saturated brine-aqueous saturated sodium hydrogen carbonate (1:1, v/v) and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=10:0.5:0.01) to obtain EM706 (71.6 mg, Yield: 16%, white powder).

EM706: m. p.: 176–179° C.

IR (KBr) v: 3468, 2966, 2852, 2360, 1736, 1718, 1558, 1462, 1379, 1246, 1165, 1126, 1099, 1076, 1038, 1016 $cm^{-1}$.

HRMS (FAB)m/z: $C_{33}H_{56}NO_{11}[M+H]^+$ Calculated 642.3853 Found 642.3866.

Example 31

Synthesis of de(3'-N-methyl)-de[12-(1-hydroxypropyl)]-8,9-anhydro-pseudoerythromycin A 6,9-hemiketal (EM751)

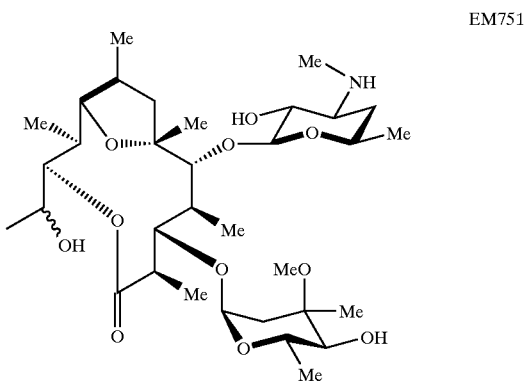

EM751

Sodium borohydride (22.9 mg, 0.605 mmol) was added to methanol (3.0 mL)solution of EM706(38.8 mg, 0.0605 mmol) at 0° C. and stirred for 1 hour. After confirming completion of the reaction by TLC, the reaction was terminated by adding acetone (0.5 mL), and the reaction mixture was diluted with saturated brine-aqueous saturated sodium hydrogen carbonate (1:1, v/v) and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM751 (31.4 mg, Yield: 81%, white powder).

EM751: m. p.: 123–125° C.

IR (KBr) v: 3504.0, 2448.1, 2971.8, 2935.1, 1729.8, 1664.3, 1594.8, 1457.9, 1378.9, 1334.1, 1265.1, 1166.7, 1126.2, 1078.0, 1041.4, 1016 $cm^{-1}$.

HRMS (FAB)m/z: $C_{33}H_{58}NO_{11}[M+H]^+$ Calculated 644.3987 Found 644.4011

Example 32

Synthesis of de(3-O-cladinosyl) -de(3'-N-methyl) -8,9-anhydrous-pseudoerythromycin A 6,9-hemiketal (EM754)

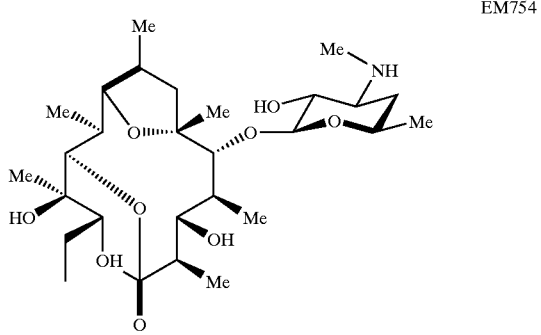

EM754 p-toluenesulfonic acid monohydrate (53.9 mg, 0.283 mmol) was added to dimethylformamide (3.8 mL) solution of EM703 (132.4 mg, 0.189 mmol) and stirred at 50° C. for 6 hours. After confirming completion of the reaction by TLC, the reaction mixture was diluted with water, adjusted to pH 8 by adding saturated aqueous sodium hydrogen carbonate and extracted with dichloromethane. The organic layer was dehydrated by adding sodium sulfate, filtered to remove the sodium sulfate, and removed the solvent to obtain crude substance. The crude substance was purified by silica gel column chromatography (chloroform:methanol:aqueous ammonia=15:1:0.1) to obtain EM754 (50.2 mg, Yield: 49%, white powder).

EM754: m. p.: 218–221° C.

IR (KBr) ν3432.7, 2969.8, 2927.4, 2858.0, 1708.6, 1629.6, 1457.9, 1405.9, 1380.8, 1319.1, 1270.9, 1232.3, 1130.1, 1078.0, 1039.4cm$^{-1}$.

HRMS (FAB)m/z: $C_{28}H_{49}NO_9Na$ [M+Na]$^+$ Calculated 566.3305 Found 566.3311.

Effect of the Invention

Novel pseudoerythromycin of the present invention has decreased antibacterial activity and increased antiinflammatory action, and is expected as the novel antiinflammatory agent.

What is claimed is:

1. A pseudoerythromycin derivative represented by the general formula [I],

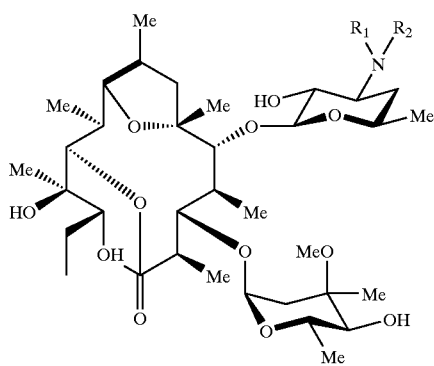

[I]

wherein
- $R_1$ is selected from the group consisting of H, alkyl, alkynyl, acyl, or sulfonyl;
- $R_2$ is selected from the group consisting of H, alkyl, alkynyl, acyl, or sulfonyl;
- Me indicates methyl; and compounds wherein each of $R_1$ and $R_2$ are both H, methyl, ethyl, or propyl are excluded.

2. A compound according to claim 1 which is de(3'-N-methyl)-3'-N-sulfonyl-8,9-anhydro-pseudoerythromycin A 6,9-hemiketal or salt thereof.

3. A compound according to claim 1 which is de(3'-N-methyl)-[3'-N-(3-hydroxy-1-propyl)]-8,9-anhydro-pseudoerythromycin A 6,9-hemiketal or salt thereof.

4. A compound according to claim 1 which is de(3'-N-methyl)-3'-N-(2-acetoxyethyl)-8,9-anhydro-pseudoerythromycin A 6,9-hemiketal or salt thereof.

5. A compound according to claim 1 which is de(3'-N-methyl)-3'-N-cyanomethyl-8,9-anhydro-pseudoerythromycin A 6,9-hemiketal or salt thereof.

6. A compound according to claim 1 which is de(3'-N-methyl)-3'-N-(2-fluoroethyl)-8,9-anhydro-pseudoerythromycin A 6,9-hemiketal or salt thereof.

7. A compound according to claim 1 which is bis-de(3'-N-methyl)-3'-N-allyl-8,9-anhydro-pseudoerythromycin A 6,9-hemiketal or salt thereof.

8. A compound according to claim 1 which is bis-de(3'-N-methyl)-3',3'-N,N-diallyl-8,9-anhydro-pseudoerythromycin A 6,9-hemiketal or salt thereof.

9. A compound according to claim 1 which is bis-de(3'-N-methyl)-3'-N-propargyl-8,9-anhydro-pseudoerythromycin A 6,9-hemiketal or salt thereof.

10. A compound according to claim 1 which is bis-de(3'-N-methyl)-3',3'-N,N-dipropargyl-8,9-anhydro-pseudoerythromycin A 6,9-hemiketal or salt thereof.

11. A compound according to claim 1 which is bis-de(3'-N-methyl)-3'-N-hexyl-8,9-anhydro-pseudoerythromycin A 6,9-hemiketal or salt thereof.

12. A compound according to claim 1 which is bis-de(3'-N-methyl)-3',3'-N,N-dihexyl-8,9-anhydro-pseudoerythromycin A 6,9-hemiketal or salt thereof.

13. A compound according to claim 1 which is bis-de(3'-N-methyl)-3'-N-benzyl-8,9-anhydro-pseudoerythromycin A 6,9-hemiketal or salt thereof.

14. A compound according to claim 1 which is bis-de(3'-N-methyl)-3',3'-N,N-dibenzyl-8,9-anhydro-pseudoerythromycin A 6,9-hemiketal or salt thereof.

15. A compound according to claim 1 which is bis-de(3'-N-methyl)-3',3'-N,N-di-(10-bromo-1-decanyl)-8,9-anhydro-pseudoerythromycin A 6,9-hemiketal or salt thereof.

16. A compound according to claim 1 which is bis-de(3'-N-methyl)-3'-N-acetyl-8,9-anhydro-pseudoerythromycin A 6,9-hemiketal or salt thereof.

17. A pseudoerythromycin derivative represented by the formula [II],

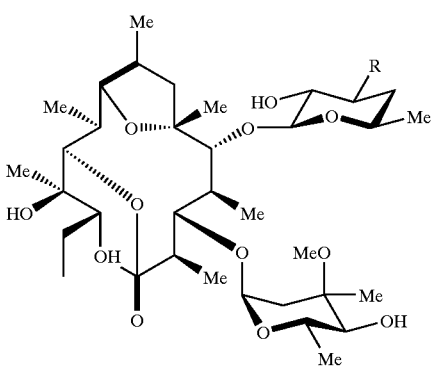

[II]

wherein R is a heterocyclic group containing N in a ring having 4 to 6 carbon atoms with a N bound within said ring, and Me indicates methyl.

18. A compound according to claim 17 which is de(3'-dimethylamino)-3'-piperidino-8,9-anhydro-pseudoerythromycin A 6,9-hemiketal or salt thereof.

19. A compound according to claim 17 which is de(3'-dimethylamino)-3'-pyrrolidino-8,9-anhydro-pseudoerythromycin A 6,9-hemiketal or salt thereof.

20. A compound according to claim 17 which is de(3'-dimethylamino)-3'-morpholino-8,9-anhydro-pseudoerythromycin A 6,9-hemiketal or salt thereof.

21. A compound according to claim 17 which is de(3'-dimethylamino)-3'-[hexahydro-1(1H)-azepinyl]-8,9-anhydro-pseudoerythromycin A 6,9-hemiketal or salt thereof.

22. A pseudoerythromycin derivative represented by the formula [III],

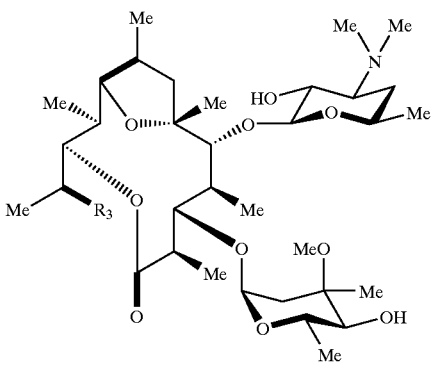

wherein $R_3$ is NOH, and Me indicates methyl.

23. A compound according to claim 22 which is de(12-hydroxy)-de[12-(1-hydroxypropyl)]-12-hydroxyoxime-8,9-anhydro-pseudoerythromycin A 6,9-hemiketal or salt thereof.

24. A pseudoerythromycin derivative represented by the formula [IV],

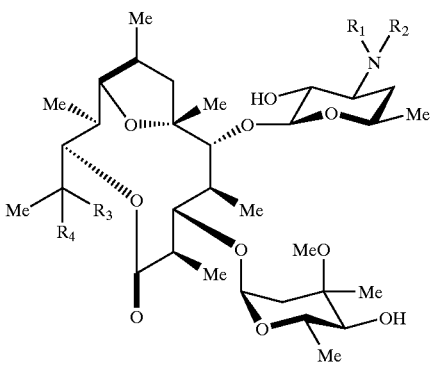

wherein $R_1$ and $R_2$ are same or different and each represents H or methyl, $R_3$ and $R_4$ represent H, hydroxyl or amino, and Me indicates methyl.

25. A compound according to claim 24 which is de[12-(1-hydroxypropyl)]-8,9-anhydro-pseudoerythromycin A 6,9-hemiketal or salt thereof.

26. A compound according to claim 24 which is de(12-hydroxy)-de[12-(1-hydroxypropyl)]-12-amino-8,9-anhydro-pseudoerythromycin A 6,9-hemiketal or salt thereof.

27. A compound according to claim 24 which is de(3'-N-methyl)-de [12-(1-hydroxypropyl)]-8,9-anhydro-pseudoerythromycin A 6,9-hemiketal or salt thereof.

28. A pseudoerythromycin derivative represented by the formula [V],

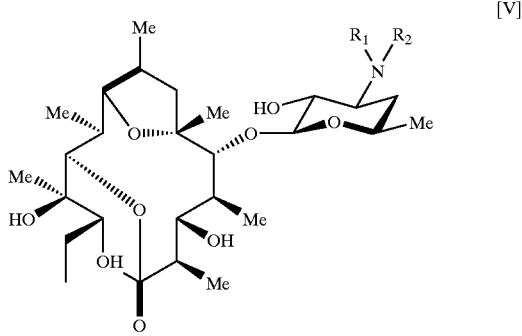

wherein $R_1$ and $R_2$ are same or different and each represents H or methyl, and Me indicates methyl.

29. A compound according to claim 28 which is de(3-O-cladinosyl)-8,9-anhydro-pseudoerythromycin A 6,9-hemiketal or salt thereof.

30. A compound according to claim 28 which is de(3-O-cladinosyl)-de(3'-N-methyl)-8,9-anhydro-pseudoerythromycin A 6,9-hemiketal or salt thereof.

* * * * *